United States Patent [19]

Mendelson et al.

[11] Patent Number: 5,137,023
[45] Date of Patent: Aug. 11, 1992

[54] METHOD AND APPARATUS FOR MONITORING BLOOD ANALYTES NONINVASIVELY BY PULSATILE PHOTOPLETHYSMOGRAPHY

[75] Inventors: Yitzhak Mendelson, Worcester; Robert A. Peura, Princeton, both of Mass.; Hannu Harjunmaa, Vessy, Switzerland

[73] Assignee: Worcester Polytechnic Institute, Worcester, Mass.

[21] Appl. No.: 511,229

[22] Filed: Apr. 19, 1990

[51] Int. Cl.$^5$ .............................................. A61B 5/00
[52] U.S. Cl. ..................................... 128/633; 128/664
[58] Field of Search ........................... 128/632–634, 128/664, 666; 356/39–41; 250/215

[56] References Cited

U.S. PATENT DOCUMENTS

| | | |
|---|---|---|
| 1,758,088 | 5/1930 | Schmick . |
| 2,721,942 | 10/1955 | Friel et al. . |
| 3,463,142 | 8/1969 | Harte . |
| 3,638,640 | 2/1972 | Shaw . |
| 3,926,527 | 12/1975 | Pembrook et al. . |
| 3,958,560 | 5/1976 | March . |
| 3,963,019 | 6/1976 | Quandt . |
| 4,029,085 | 6/1977 | DeWitt et al. ............... 128/2 R |
| 4,033,330 | 7/1977 | Willis et al. . |
| 4,169,676 | 10/1979 | Kaiser . |
| 4,266,554 | 5/1981 | Hamaguri . |
| 4,267,844 | 5/1981 | Yamanishi . |
| 4,306,877 | 12/1981 | Lübbers . |
| 4,321,930 | 3/1982 | Jöbsis et al. . |
| 4,380,240 | 4/1983 | Jöbsis et al. . |
| 4,398,541 | 8/1983 | Pugliese . |
| 4,427,889 | 1/1984 | Müller . |
| 4,485,820 | 12/1984 | Flower . |
| 4,513,751 | 4/1985 | Abe et al. . |
| 4,570,638 | 2/1986 | Stoddart et al. . |
| 4,586,513 | 5/1986 | Hamaguri . |
| 4,603,700 | 8/1986 | Nichols et al. . |
| 4,621,643 | 11/1986 | New, Jr. et al. . |
| 4,641,658 | 2/1987 | Lepper ....................... 128/633 |
| 4,653,498 | 3/1987 | New, Jr. et al. . |
| 4,655,225 | 4/1987 | Dähne et al. . |
| 4,704,029 | 11/1987 | Van Heuvelan . |
| 4,725,147 | 2/1988 | Stoddart . |
| 4,750,496 | 6/1988 | Reinhart et al. . |
| 4,759,369 | 7/1988 | Taylor . |
| 4,768,516 | 9/1988 | Stoddart et al. . |
| 4,796,636 | 1/1989 | Branstetter et al. . |
| 4,805,623 | 2/1989 | Jöbsis . |
| 4,817,623 | 4/1989 | Stoddart et al. . |
| 4,832,484 | 5/1989 | Aoyagi et al. . |
| 4,882,492 | 11/1989 | Schlager . |
| 5,028,787 | 7/1991 | Rosenthal et al. ............... 250/341 |
| 5,054,487 | 10/1991 | Clarke ........................ 128/633 |

FOREIGN PATENT DOCUMENTS

0160768  4/1984  Switzerland .
WO90/07905  1/1990  World Int. Prop. O. .

OTHER PUBLICATIONS

"Blood Glucose Sensors: An Overview" by R. A. Peura and Y. Mendelson—1984 pp. 63–68.
Harjunmaa et al., Ser. No. 7/511,341, Apr. 19, 1990.

Primary Examiner—Kyle L. Howell
Assistant Examiner—Kevin Pontius
Attorney, Agent, or Firm—Hamilton, Brook, Smith & Reynolds

[57] ABSTRACT

A non-invasive system for measuring the concentration of an analyte, such as glucose, in an absorbing matrix is described. The system directs beams of light at the matrix using an analyte sensitive wavelength and an analyte insensitive wavelength. The principles of photoplethysmography are applied to measure the change in light intensity caused by matrix absorption before and after the blood volume change caused by the systolic phase of the cardiac cycle. The change in light intensity is converted to an electrical signal which is used to adjust the light intensity and as a measure of analyte concentration.

7 Claims, 2 Drawing Sheets

METHOD AND APPARATUS FOR MONITORING BLOOD ANALYTES NONINVASIVELY BY PULSATILE PHOTOPLETHYSMOGRAPHY

BACKGROUND OF THE INVENTION

One the most common techniques for measuring blood glucose requires removal and subsequent analysis of a sample of the patients blood using reagent-strip reflectance photometry. This technique is still considered to be the most accurate method for obtaining an absolute reading of blood glucose. However, this technique is painful and also undesirable in cases where it is necessary to monitor blood glucose continuously over long periods of time and preferably noninvasively. Moreover, the reagent-strip method is known to be technique sensitive (both in terms of the method used to read the reagent strip and source of blood used for the analysis, i.e., capillary, venous or arterial blood). Furthermore, instrument calibration at the factory may drift in the field due to the decay in enzyme activity or humidity-mediated hydration of the strips. Most importantly, an intermittent invasive technique is not suitable for continuous monitoring of blood glucose or for controlling an artificial pancreas device which can automatically and continuously inject insulin in response to a specific demand to a diabetic patient Many methods and devices have been developed up to now for the determination of glucose in vitro or in vivo by optical means. Progress towards the development of continuous blood glucose monitoring methods is disclosed in "Blood Glucose Sensors: An Overview", by Peura R. A. and Mendelson Y., (Proceedings of the IEEE/NSF Symposium on Biosensors, 1984).

In PCT application WO No. 81/00622, there is disclosed an IR absorption method and apparatus for determining glucose in body fluids. According to this reference, absorption spectra of serum or urine, both transmissive or reflective, i.e., due to back-scattering effects, are measured at two distinct wavelengths $\lambda_1$ and $\lambda_2$. $\lambda_1$ being typical of the substance of interest and $\lambda_2$ being roughly independent of the concentration of the substance of interest. Then the pertinent measured data are derived from calculating the ratio of the absorption values at $\lambda_1$ and $\lambda_2$, the bands of interest being in the range of 940-950 $cm^{-1}$ (10.64-10.54 $\mu m$) and 1090-1095 $cm^{-1}$ (9.17-9.13 $\mu m$), respectively. In this reference, the source of irradiation is provided by a $CO_2$ laser.

Swiss Patent No. CH-612.271 discloses a non-invasive method to determine biological substances in samples or through the skin using an attenuated total reflection (ATR) prism directly placed against a sample to be analyzed (for instance the lips or the tongue). The refractive index of the wave-guide being larger than that of the sample (optically thinner medium), the beam propagates therein following a totally reflected path. The only interaction thereof with the thinner medium (to be analyzed) being that of the "evanescent wave" component at the reflection interface (See also Hormone & Metabolic Res/suppl. Ser. (1979), p. 30-35). When using predetermined infrared wavelengths typical of glucose absorption, the beam in the ATR prism is attenuated according to the glucose concentration in the optically thinner medium. This attenuation is ascertained and processed into glucose determination data.

U.S. Pat. No. 3,958,560 discloses a non-invasive device for determining glucose in a patient's eye. The device comprises a contact-lens shaped sensor device including an infrared source applied on one side of the cornea and a detector on the other side thereof. Thus, when infrared radiation is applied to the area being measured, light is transmitted through the cornea and the aqueous humor of the eye to the detector. The detected signal is transmitted to a remote receiver and a read-out device providing data on the concentration of glucose in the patient's eye as a function of the specific modifications undergone by the IR radiations when passing through the eye.

GB Patent Application No. 2,033,575 discloses a detector device for investigating substances in a patient's blood stream, namely $CO_2$, oxygen or glucose. The key features of such a detector comprises use of radiation directed into the patient's body, and receiving the attenuated optical radiations backscattered or reflected within the patients body i.e., from a region below the skin surface. The detected signal is thereafter processed into useful analytical data. Optical radiations include UV as well as IR radiations.

Other references refer to the measurement or monitoring of other bioactive parameters and components such as blood flow, oxyhemoglobin and deoxy hemoglobin. Because of their close analogies with the aforementioned techniques, they are also worth reviewing here.

U.S. Pat. No. 3.638,640 discloses a method and an apparatus for measuring oxygen and other substances in blood and living tissues. The apparatus comprises radiation sources and detectors disposed on a patient's body, for instance about the ear to measure the intensity passing therethrough or on the forehead to measure the radiation reflected therefrom after passing through the blood and skin tissue. The radiations used belong to the red and very near infrared region, for instance wavelengths of 660, 715 and 805 nm. The number of different wavelengths used simultaneously in the method is equal to the total of at least one measuring wavelength typical for each substance present in the area under investigation (including the substance(s) to be determined) plus one. By an appropriate electronic computation of the signals obtained after detection from absorption at these diverse wavelengths useful quantitative data on the concentration of the substance to be measured are obtained irrespective of possible changes in certain of the measurement conditions such as displacement of the test appliance, changes in illumination intensity and geometry, changes in the amount of blood perfusing the tissue under investigation and the like.

GB Patent Application No. 2,075,668 describes a spectrophotometric apparatus for measuring and monitoring in-vivo and non-invasively the metabolism of body organs, e.g., changes in the oxido-reduction state hemoglobin and cellular cytochrome as well as blood flow rates in various organs such as the brain, heart, kidney and the like. The above objects are accomplished by optical techniques involving wavelengths in the 700-1300 nm range which have been shown to effectively penetrate the body tissues down to distances of several mm. Thus in FIG. 14 of that reference there is disclosed a device involving reflectance type measurements and comprising a light source for injecting light energy into a waveguide (optical fiber bundle) applied to the body and disposed in such a way (slantwise relative to the skin) that the directionally emitted energy which penetrates into the body through the skin is reflected or backscattered by the underlying tissue to be analyzed at some distance from the source. The partially absorbed energy then reaches a first detector placed also over the skin and somewhat distantly from the source Another detector placed coaxially with the source picks up a back radiated reference signal. Both the analytical and reference signals from the detectors are fed to a computing circuit, the output of which provides useful readout data concerning the sought after analytical information.

Although the aforementioned techniques have merit some difficulties inherent thereto still exist. These difficulties are mainly related to the optical properties of the radiations used for making the measurements. Thus, radiation penetration into the skin depends on the action of absorbing chromophores and is wavelength-dependent, i.e., the light in the infrared range above 2.5 $\mu m$ is strongly absorbed by water and has very little penetration capability into living tissues containing glucose and, despite the highly specific absorption of the latter in this band, it is not readily usable to analyze body tissue volumes at depths exceeding a few microns or tens of microns. If exceptionally powerful sources (i.e., $CO_2$ laser) are used, deeper penetration is obtained but at the risk of burning the tissues under examination. Conversely, using wavelengths below about 1 $\mu m$ (1000 nm) has the drawback that, although penetration in this region is fairly good, strong absorbing chromophores still exist such as hemoglobin, bilirubin and melanin. By comparison specific absorptions due to glucose are extremely weak which provides insufficient sensitivity and accuracy for practical use in the medical field. In addition, the ATR method which tries to circumvent the adverse consequences of the heat effect by using the total internal reflection technique only enables investigation to depths of tissues not exceeding about 10 $\mu m$ which is insufficient to obtain reliable glucose determination information.

U.S. Pat. No. 4,655,225 describes a method for the spectrophotometric determination of glucose in the blood stream or tissue by measuring the optical near infrared absorption of glucose at 1575, 1765, 2100 and 2270+or −15 nm where typical glucose absorption bands exists. The measured values are compared with reference values obtained in the range of 1100 to 1300 nm or in narrow regions situated on both sides of the measuring bands but outside the area where glucose absorbs strongly and where the errors due to background absorptions by the constituents of the surrounding tissues or blood containing the glucose are of reduced significance or can be quantitatively compensated.

Although the above referenced patent has merit some difficulties inherent in the technique still exist. These difficulties are related to the near infrared optical absorption properties of glucose and water. FIG. 4 of the above reference patent U.S. Pat. No. 4,655,225, shows the change in optical density plotted as a function of glucose concentration between 0 and 1.0 mol/l for two selective wavelengths of 2100 and 1100 nm. That figure indicates correctly that the optical absorption of glucose measured at near infrared wavelengths of 2098 nm increases proportionally with glucose concentration. It furthermore indicates that the optical absorption of glucose measured at a near infrared wavelength of 1100 nm decreases slightly with glucose concentration. But it is also apparent from this figure that for normal physiological glucose concentrations, which are generally in the range between 80-110 mg/dl (0.004–0.006 mol/1), the change in optical density measured at a near infrared wavelength of 2098 is extremely small. Furthermore, even for a higher glucose concentration typically found in diabetic patients (300–600 mg/dl or 0.0166–0.033 mol/1), the change in the optical density is still small. Therefore, if the technique disclosed in the above patent is utilized as indicated, in practice, an extremely small signal change would be measured by the optical detector and then processed by electronic circuitry. Thus, the signal to noise ratio will be a major limiting factor in the practical implementation of the techniques of U.S. Pat. No. 4,655,225 as a non-invasive glucose analyzer for measuring the concentration of glucose found in humans. Furthermore, in addition to the near infrared absorption of glucose as shown in FIG. 4 of that embodiment, the light intensity either transmitted through or reflected from tissue at this characteristic wavelength will be even smaller than shown because of the presence of other absorbing components in the blood and interstitial fluid such as proteins and other tissue constituents which absorb radiation at this selected wavelength.

SUMMARY OF THE INVENTION

This invention is described as applied to the special case of glucose measurement in vivo using near infrared radiation. This should in no way detract from the general application of this invention to measure the concentration of any substance in the blood that absorbs electromagnetic radiation, especially in the presence of strongly absorbing substances, such as water, and/or a scattering media such as whole blood and biological tissues.

As noted above, in conventional measurements of near infrared transmission or reflection from biological samples (invasive as well as noninvasive), the well known optical absorption of water in the infrared spectral range is so intense that it obscures the spectral detail of other absorbing components of interest, such as glucose or cholesterol, which has a much weaker absorption band. Furthermore, the concentration of certain blood components of interest are much lower than the concentrations of other components typically found and analyzed by conventional near infrared spectroscopy. The desired signal thus becomes difficult to detect because it is masked or obscured by noise from the background absorbents. The present invention discloses a method for substantially improving the signal to noise ratio of the measurement, such that an accurate measurement of certain blood analytes (e.g., glucose, cholesterol, etc.) can be made noninvasively. Although the present invention describes a specific optical method for measuring glucose in human tissue, it should in no way detract from the general applicability of the invention to measure the concentration of any substance that absorbs electromagnetic radiation, especially in strongly absorbing and turbid media in which the substance is present.

The present invention is based on the principle of transmission and reflection photoplethysmography. Plethysmography refers to the measurement of change in volume of a part of the body. In the present invention the glucose measurement is made by analyzing either the difference or the ratio of two different near infrared radiations that are either transmitted through an appendage, or reflected from tissue surface before and after blood volume change occurring in the systolic and diastolic phases of the cardiac cycle. According to the present invention an electronic circuit or a microprocessor-based instrument determines the difference between the amount of near infrared radiation absorbed by tissue during diastole and during systole. The amount of near infrared radiation absorbed at a glucose sensitive wavelength $\lambda_G$ (e.g., 2098 nm) during diastole is due primarily to the presence of glucose in the venous blood, capillary blood, interstitial fluid, intracellular fluid, and tissue and the water content in each of these compartments. The higher amount of near infrared radiation absorbed at $\lambda_G$ during systole, however, is due not only to the presence of glucose in the venous blood, capillary blood, interstitial fluid and intracellular fluid but is also a function of the additional volume of glucose and water present in the arterial blood entering the tissue. By taking the difference between these two measurements one can obtain a differential measurement which correspond to the amount of near infrared radiation absorbed by glucose and thus render the measurement independent of the amount of glucose present in other than the arterial blood component of the tissue under investigation.

Furthermore, by only analyzing the change in light absorption and not the total amount of near infrared light absorbed by tissue one is able to subtract the influence of the near infrared radiation absorbed by bloodless tissue which is known to vary from subject to subject. For example, because of different anatomical and pathophysiological differences in skin characteristics one subject may absorb more or less radiation than another. It also allows one to substantially amplify the alternating signal component and thus achieve a much higher measurement resolution.

DETAILED DESCRIPTION OF THE INVENTION

Figure 1:
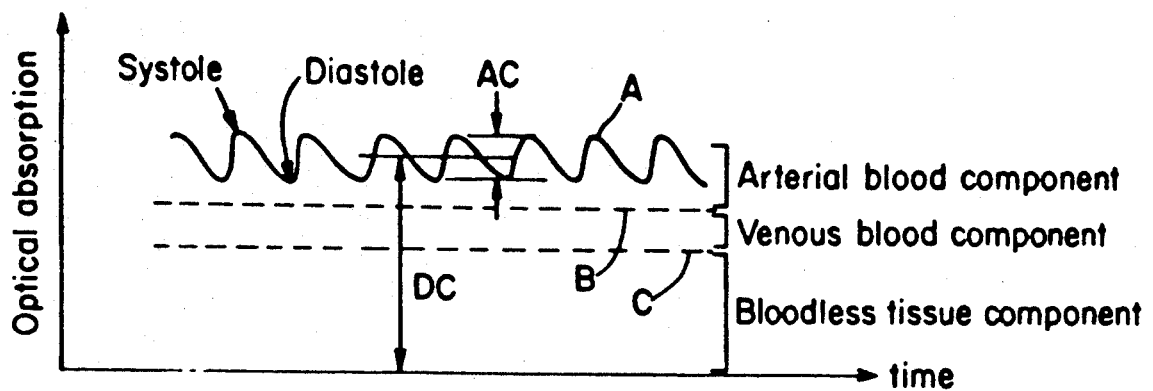
FIG. 1 is a plot of, optical absorption by vascular body tissue versus time, illustrating the variation in light intensity in phase with the change in arterial blood volume.

The major relevance of photoplethysmography to the determination of blood glucose is that the change in the absorption of the incident light is specifically caused by the pulsating arterial blood component. The absorption of light by the "non-blood" components (e.g., skin bone, etc.) does not change with pulsation as illustrated in FIG. 1 which is a plot of optical absorption of light in living tissue versus time.

The solid line of curve A shows the absorption variation over time in phase with the change in arterial blood volume. The dotted line, curve B indicates the light absorbing contributions of the venous blood which is a time-invariant parameter; while the dotted line C shows the absorbing contribution of the remaining blood-type body tissue. The resulting alternating signal is thus composed of a time-variant (AC) and a time-invariant (DC) part. Note that in FIG. 1 the magnitude of the AC signal (curve A) was magnified relative to the magnitudes of DC components B and C. This was deliberately done for clarification purposes since, in practice, the AC signal is much smaller than the DC signal.

The basic assumption underlying the hypothesis of this invention is that by measuring the difference, or the ratio of the amplitudes of the AC light intensity signals that are either transmitted through, or reflected from, a vascular tissue bed at a wavelength $\lambda_G$, which is sensitive to glucose, and another reference wavelength $\lambda_R$ which is isobestic (that is, the absorption by the tissue and blood is independent of glucose), it is possible to obtain a quantitative estimation of blood glucose concentration noninvasively.

Figure 2A:
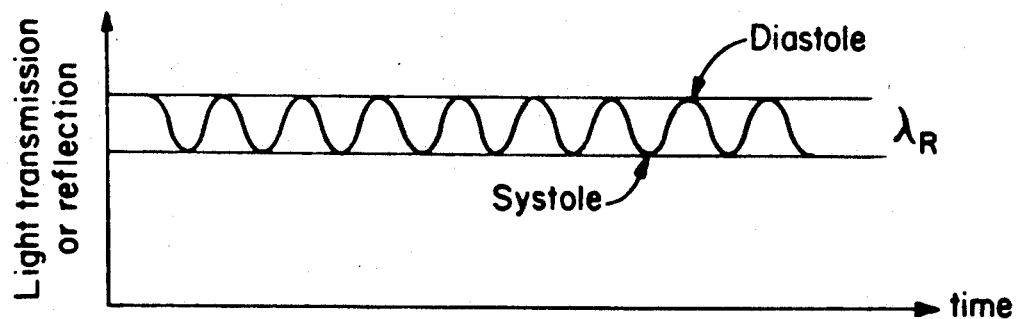
FIG. 2(a) is a plot of light transmission or reflection versus time through a vascular tissue bed at wavelengths $\lambda_R$, which is a wavelength at which the absorption by tissue and blood is independent of glucose.
Figure 2B:
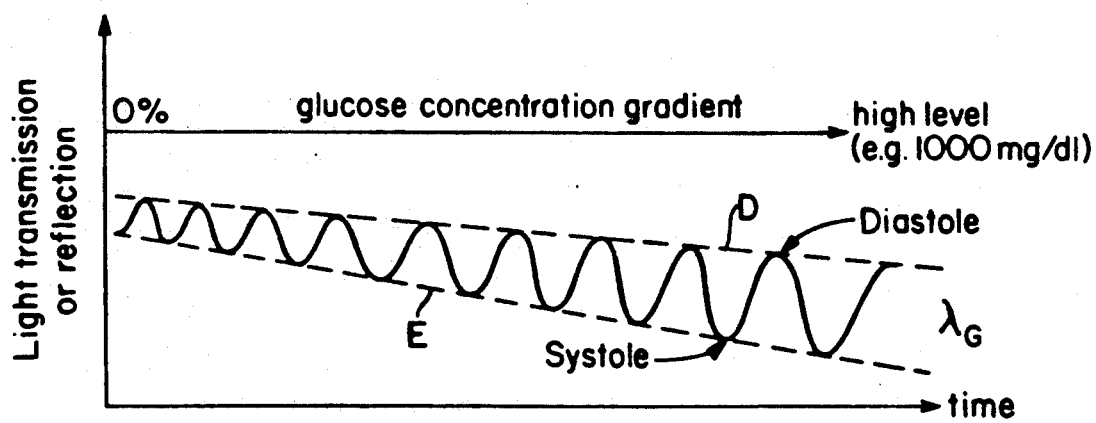
FIG. 2(b) is a plot of light transmission or reflection versus time through a vascular tissue bed at wavelengths $\lambda_G$, which is a wavelength at which the absorption by tissue and blood is sensitive to glucose.

This principle is further illustrated in the plots of FIG. 2a and FIG. 2b wherein it is assumed that blood contains only a single near infrared absorbing component such as glucose. Assuming that the change in arterial blood pulsation and the absorption of light by the nonperfused tissue components remains constant, the change in the transmitted or reflected light versus arterial blood glucose concentration can be analyzed as follows. As the blood glucose level decreases, the absorption at $\lambda_G$ decreases too. This results in a higher DC light intensity transmitted or reflected from the tissue as indicated by the tangent lines E and D joining the respective peak systolic and peak diastolic events in FIG. 2b. Note also that the slope of these two lines is different. During diastole, most of the light is absorbed by the venous blood. During systole, in addition to the absorption by the venous blood, radiation is also absorbed by the arterial blood depending on the blood glucose level. Thus, the combined attenuation of light by both venous and arterial blood present in the tissue leads to further reduction in the increases. Accordingly, the amplitudes of the photoplethysmograms corresponding to the $\lambda_G$ wavelength increases as glucose is increased. Note also that this relationship is in contrast to that observed when arterial oxygen saturation is measured using the principle of transmission or reflection pulse oximetry.

Furthermore, in the measurement of oxygen saturation by pulse oximetry, the additional light absorbed by the blood during systole is due to the increase in the content of red blood cells containing hemoglobin in the tissue; whereas in the present invention, the observed increase in the infrared absorption during systole is due to the increase in the plasma content containing glucose.

Blood contains a number of near infrared absorbing components besides glucose such as cholesterol, urea, albumin, etc. In addition, the spectral location and magnitude of the near infrared absorption peaks are temperature dependent. Therefore, in order to improve the accuracy of the measurement, it is important to perform the measurement under constant temperature conditions, preferable, but not limited to, the temperature range between 37° and 38° C. This temperature range is compatible with the physiological temperature range of blood in normal healthy subjects.

Figure 3:
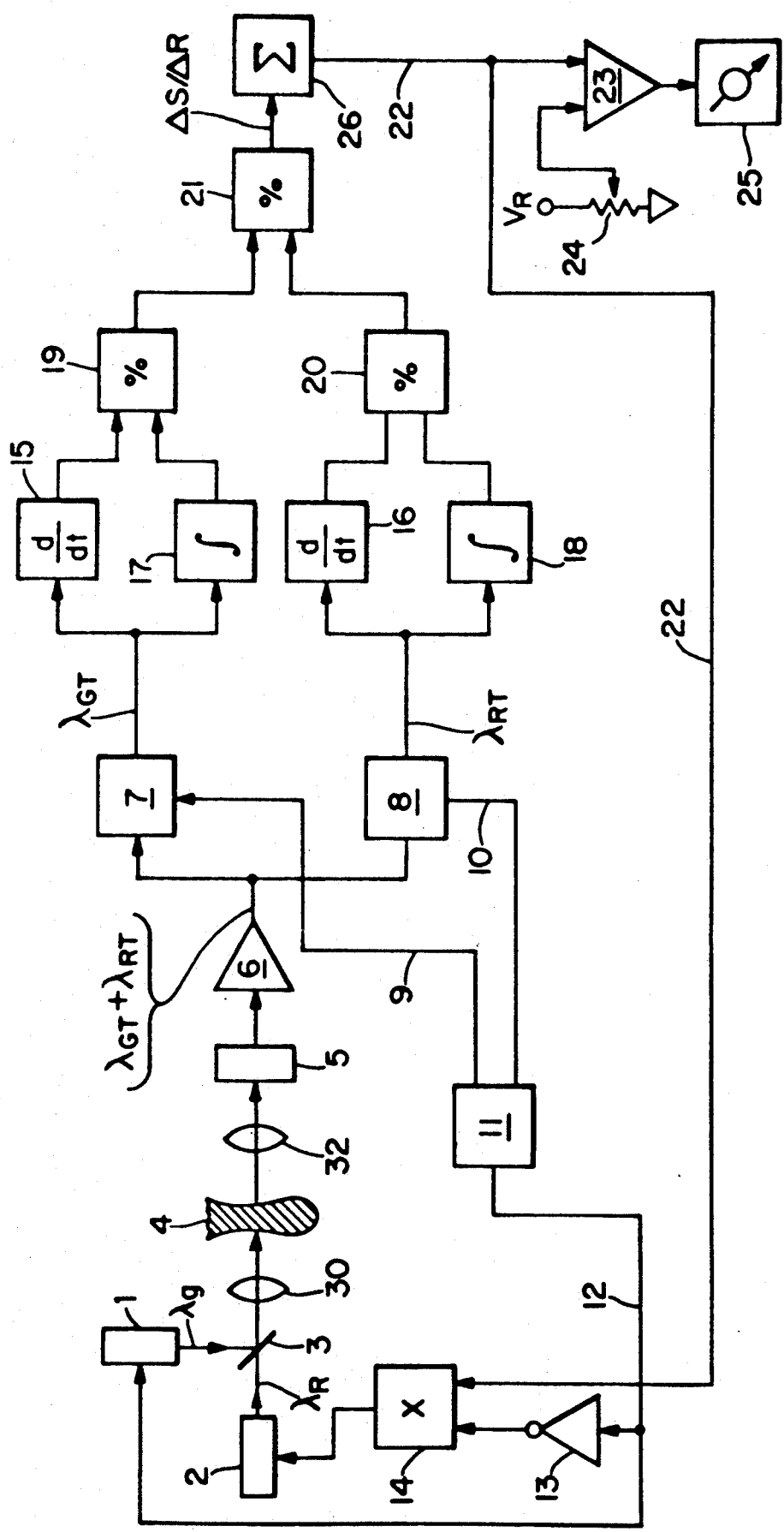
FIG. 3 is a block diagram of an apparatus for measuring the glucose concentration of a subject in accordance with the invention.

Referring now to FIG. 3, a preferred embodiment of the invention will now be described in detail. The radiation source of this example consists of two monochromatic light sources (e.g., lasers) (1, 2) operating at the wavelengths $\lambda_G$ and $\lambda_R$, respectively. The output beams of the lasers are combined in the beam combiner (3).

The combined beam is directed into a sample (4), such as an earlobe.

The optical system includes collimating means, (30, 32) i.e., lenses or mirrors to direct the sample channel beam into the sample (4) and from the sample (4) to the sample channel detector (5).

The system of FIG. 3 uses a photoconductive PbS infrared detector (5) operating at room temperature. Its spectral sensitivity peaks at about 2.0 to 2.5 μm. The PbS detector (5) is operated in the classical bolometer circuit, AC-coupled to a pre-amplifier (6). Any other detector sensitive in the relevant wavelength range could be used, with the appropriate coupling and amplifying method. The output of the pre-amplifier (6) is a time-multiplexed signal composed of the two radiation powers transmitted sequentially by the sample (4).

The radiation powers transmitted by the sample (4) for each of the two incident wavelengths are first demultiplexed by passing the signal from the pre-amplifier (6) through two sample and hold circuits (7) and (8). These two sample and hold circuits are synchronously triggered by short gate pulses (9) and (10), respectively, which are generated by the timing circuitry (11). The timing circuitry (11), which can be a simple square wave generator, also generates a switching signal (12) that alternatively turns the two lasers (1) and (2) "On" and "Off", respectively.

The output of the two sample and hold circuits (7) and (8) is thus a continuous signal proportional to the AC and DC parts of the two photoplethysmographic signals produced by the photodetector. Thus the output of the two sample and holds circuits (7) and (8) generates two channels representing the radiation transmitted at the two wavelengths $\lambda_{GT}$ and $\lambda_{RT}$ respectively.

The operation of the system is governed by the square wave generator (11) operating at a frequency of typically between 100 Hz and 1 kHz. Its output determines which one of the two wavelengths and which one of the two corresponding intensity levels is to be used. It is assumed that the output of the lasers are proportional to intensity control voltages (if the control voltage is zero, then the laser beam is Off). If in a particular embodiment the lasers (1) and (2) are of a type whose intensity cannot be controlled by a voltage, then an appropriate modulator is used to the same effect. The inverter (13) between timing circuit (11) and analog multiplexer (14) ensures that the lasers (1) and (2) operated in antiphase, or that one of them is "Off" while the other is "On".

The analog multiplier (14) changes the intensity of the beam between the two intensity values produced by the passage of the different wavelength beam through the tissue and adjusts one of the intensities according to the output of the control signal (22). In the difference technique, as long as that output is non-zero, the intensity is constantly adjusted to zero the output (22). If a ratiometric technique is employed, instead of the difference technique, as long as that output is not equal to unity, the intensity is constantly adjusted to cause the output (22) to reach unity.

The outputs of the two sample and hold circuits (7) and (8) are fed simultaneously to differentiator circuits (15),(16) and integrator circuits (17) and (18). Thus, for example, the composite AC and DC signal corresponding to the radiation detected for the $\lambda_G$ wavelength is decomposed into an AC component by differentiator (15) and into an DC component by the integrator (17). Likewise, the composite AC and DC signal corresponding to the radiation detected for the $\lambda_R$ wavelength is decomposed into an AC component by differentiator (16) and into a DC component by the integrator (18).

The AC and DC signals corresponding to the two radiations detected by the detector can further be processed for example by respective electronic ratio circuits (19 and 20) which generate a normalized ratio signal equal to the AC/DC signal for each wavelength. Finally, the two output signals generated by the ratio circuits (19) and (20) are fed to an electronic circuit (21) which generates an error signal, i.e., ΔS or ΔR depending on whether a differential or ratiometric technique is employed as outlined above. The error signal is then integrated in an active integrator (26) to produce a control signal (22).

During operation, the control signal (22) servoes itself to zero or unity depending on the method selected for implementation. The intensity control signal (22) is used as the basis of the glucose concentration display by setting its zero or unity point by comparison, in the difference amplifier (23), with the voltage setting of a voltage divider circuit formed of potentiometer (24) and reference voltage $V_R$. The resulting voltage is scaled and displayed continuously by the display unit (25) to show the glucose concentration of the patient.

The present invention thus comprises an apparatus for measuring the glucose concentration of a subject and consists in general of a light source (for example a laser or other light source such as a quartz halogen lamp), means for selecting multiple infrared wavelengths from the light source (for example narrow band optical interference filters or a monochromator), means for alternately directing the monochromatic light beam at the selected wavelengths to a portion of the subject's body (for example a chopper wheel and a fiber optic bundle), means for detecting the amount of near infrared radiation either transmitted through (for instance through the ear lobe, finger tip) or reflected (backscattered) from (for example the forehead, forearm, etc.) the subject's body segment (for example lead sulfide (PbS). germanium (Ge) or Indium Gallium Arsenide (InGaAs) detector, means for analyzing the detected light intensity, such as, an electronic circuit or a microprocessor for determining glucose concentration according to a predetermined mathematical relationship, and means for displaying the concentration of glucose computed by the electronic circuitry. One characteristic feature of the present invention is that it comprises means for detecting the change in the amount of near infrared radiation absorbed by tissue during the inflow phase of the arterial blood pulse associated with the systolic action of the heart.

The actual measurement of glucose is performed in four steps. First, transmission or reflection photoplethysmograms each consisting of an AC and a corresponding DC component are produced for each of the infrared wavelengths employed. Second, for each of the infrared wavelengths, a ratio between the AC and DC components of the corresponding photoplethysmograms is formed producing a so called "normalized ratio". Third, a null signal which is close to zero or unity depending upon whether a difference or a ratiometric technique is employed, is formed. Fourth, a reading of glucose concentration is performed by analyzing the change in the null signal for a variable non-zero glucose concentration.

A significant difference between the method described here and those known in the art is the method used to achieve the improved sensitivity in detecting lower glucose concentrations in the presence of a highly absorbing background component, such as water. Specifically, this is related to the selection of the wavelengths $\lambda_G$ and $\lambda_R$ and subsequently calibrating the readings of the system. This is accomplished by preselecting a fixed glucose sensitive wavelength $\lambda_G$ (for example 2.1 μm) and then fine tuning the reference wavelength $\lambda_R$ until the normalized AC/DC value of the two photoplethysmographic signals are equal. The two wavelengths are selected so that the radiation passing through or reflected from the body has exactly the same degree of matrix extinction i.e., the sum of the absorption and scattering experienced by the radiation is the same at these wavelengths).

This fine tuning can be performed manually or automatically. During the initial tuning phase, a blood sample is taken from the patient from which the concentration of glucose is determined utilizing other well known accurate independent measurement techniques. The value of glucose measured during this initial calibration phase is noted and then used to establish a quantitative relationship with the value measured and displayed by the optical system. Following the initial fine tuning, the difference or the ratio of the two normalized pulsatile components of the glucose sensitive wavelength and the glucose insensitive wavelength, which is called the error signal $\Delta S$ or $\Delta R$ is representative of the change in glucose concentration. This signal, however, is not used to quantify the analyte concentration directly. It is used, instead, in a null arrangement to change the relative radiation intensity (by multiplexer 14) of one of the wavelengths, preferably the reference wavelength $\lambda_R$. A closed-loop control signal (22) is derived from the error signal $\Delta S$ or $\Delta R$ by integration in integrator (26). The value of the control signal (22) needed to restore either a zero (in the case of a difference technique) or a unity (in the case of a ratiometric approach) signal is then used as an indicator of the analyte concentration. With the method described in this invention, one can non-invasively detect lower glucose concentrations in vivo than with the currently known methods.

The principles governing the method of the present invention are briefly outlined below with the assumption that the Beer-Lambert law, $P = P_o e^{-k(\lambda)x}$ is valid.

In the above relation, P is the power of the transmitted beam, $P_o$ is the power of the incident collimated beam falling on the sample, $k(\lambda)$ is the wavelength dependent absorption coefficient (usually in cm$^{-1}$) and x is the change in path length (in cm) of the sample during systole in which interaction occurs. To simplify the equations, only essential quantities are retained and the signal is considered radiative only; scattering can be included in k, and, if its contribution is desired explicitly, it is a straightforward operation to replace k by the sum of absorption and scattering effects.

In view of the above, the powers collected at wavelengths $\lambda_G$ and $\lambda_R$ are equal to:

$$P_{\lambda(G)} = P_{o(G)} e^{-k(G)x} \text{ and } P_{\lambda(R)} = P_{o(R)} e^{-k(R)x},$$
respectively, Since provision is made that the absorption of the background is the same at $\lambda_G$ and $\lambda_R$, the difference:

$$\Delta S = P_{\lambda(G)} - P_{\lambda(R)} = 0$$
or the ratio, $$\Delta R = P_{\lambda(G)}/P_{\lambda(R)} = 1$$

if no analyte is present. This difference $\Delta S$ or ratio $\Delta R$ are hereafter called the error signals.

When an analyte is present, it absorbs at one of the wavelengths but not at the other, which means that for the first wavelength, say $\lambda_G$, the absorption coefficient has changed by, say, $\Delta k$. Hence now, $$\Delta S \neq 0 = P_o[e^{-(k-\Delta k)x} - e^{-kx}] = P_o e^{-kx}[e^{\Delta kx} - 1]$$

or $$\Delta R \neq 1 = [e^{-(k-\Delta k)x}/e^{-kx}] = e^{\Delta kx}.$$

Now for small values of x and $\Delta k$, i.e. <0.1 the known approximation $e^{\Delta kx} = 1 + \Delta kx$ holds so $\Delta S = P_o \Delta kx e^{-kx}$, or $\Delta R = 1 + \Delta kx$, i.e. the error signal is proportional to $\Delta k$, that is, to the analyte concentration.

When the concentration of analyte is nonzero, an error signal is generated, but the system strives to keep it either at zero, if a difference technique is used, or at 1, if a ratiometric technique is employed, by changing the intensity of one component length according to:

$$P_{o(R)} = (1+f)P_{o(G)}.$$

Here, f is the relative change in the intensity at $\lambda_R$ with respect to the equilibrium state. If a difference technique is employed, $$\Delta S = P_{o(G)} e^{-k(G)x} - P_{o(R)} e^{-k(R)x} = 0$$

$$P_{o(G)} e^{-k(G)x} - (1+f)P_{o(G)} e^{-k(R)x} = 0$$

$$e^{-k(G)x} = (1+f)e^{-k(R)x}$$

$$1+f = e^{\Delta kx}.$$

Similarly, for a ratiometric technique, $$\Delta R = P_{o(G)} e^{-k(G)x}/P_{o(R)} e^{-k(R)x} = 1$$

$$P_{o(G)} e^{-k(G)x}/(1+f)P_{o(G)} e^{-k(R)x} = 1$$

$$e^{-k(G)x} = (1+f)e^{-k(R)x}$$

$$1+f = e^{\Delta kx}.$$

If $\Delta kx$ is small, which is to be expected, the approximation $e^{\Delta kx} = 1 + \Delta kx$ is valid, which leads to:

$$f = \Delta kx.$$

or, the relative deviation from equilibrium intensity is proportional to analyte concentration and to the incremental change in path length during systole, x.

In order to account correctly for scattering, the wavelength choice must be made on the basis of the sum spectrum of absorption and scattering in the sample matrix (that is, extinction spectrum) with due consideration to the measuring geometry, which affects the relative importance of scattering.

Table 1 below indicates a few wavelengths, (taken from EPO 160 768) at which glucose absorbs which can be used to practice the invention in combination with the background absorption values on the same line of the Table. Water absorption coefficients at the indicated wavelengths are also in the Table.

TABLE 1

| Wavelength (μm) | Glucose Absorption (μm) | Background Absorption (μm) | kH₂O (cm⁻¹) |
|---|---|---|---|
| 1.57 | 1.75 (gl)*, | 1.38 (st)* | 9 |
| 1.77 | 1.55 (gl), | 1.39 (st) | 7 |
| 2.10 | 2.29 (gl), | 1.87 (st), 1.48 (pk)* | 30 |
| 2.17 | 1.86 (st), | 1.49 (st), 1.41 (st) | 25 |
| 2.27 | 2.15 (gl), | 1.86 (st) 1.48 (pk), 1.40 (st) | 30 | where:
*st = steep;
pk = peaking;
gl = glucose absorption.

For fine tuning the wavelengths, one keeps a member of the pair constant while the other is adjusted. Preferably the glucose wavelength is kept constant in order to have a constant sensitivity for glucose. The reference wavelength is preferably situated on a moderate or shallow slope of the water absorption spectrum With a steep slope, accurate control is more difficult In Table 1, some reference wavelengths are situated on a steep slope; others are at or near a peak; some reference wavelengths have glucose absorption. The fine tuning can be done automatically. Because of the strength of glucose absorption at 2.1 μm, the present embodiment has been devised for the wavelength pair 2.10/1.48 μm. Obviously, this wavelength's selection is only one example, no other suitable wavelength pairs being excluded from the scope of this application.

Equivalents

Those skilled in the art will know, or be able to ascertain using no more than routine experimentation, many equivalents to the specific embodiments of the invention described herein.

These and all other equivalents are intended to be encompassed by the following claims.

We claim:

1. A method for determining the concentration of glucose in the blood of a body matrix which is subject to the systolic and diastolic phases of blood flowing through the matrix during the cardiac cycle, comprising the steps of:
   a) generating a composite beam of electromagnetic radiation at each of two distinct wavelengths, a first such wavelength being glucose sensitive and a second such wavelength being glucose insensitive and wherein the two distinct wavelengths have the same matrix extinction in the body matrix and are in the infrared band of light;
   b) directing said composite radiation at said matrix;
   c) detecting said composite radiation after it has traversed a portion of said matrix; and
   d) generating a composite electrical intensity signal proportional to the intensity of the detected composite radiation, which intensity signal is comprised of an alternating component produced by the variation in volume of blood flowing through the matrix and a non-alternating component produced by the non-varying portions of the matrix;
   e) separating the composite electrical signal into a first channel signal consisting of that portion of the electrical signal produced by detecting radiation at said first wavelength and a second channel signal consisting of that portion of the electrical signal produced by detecting radiation at said second wavelength;
   f) decomposing the first channel signal into a first alternating signal and a first non-alternating signal;
   g) decomposing the second channel signal into a second alternating signal and a second non-alternating signal;
   h) determining the amplitude ratio of the alternating to the non-alternating signal of each of the first and second channel signals;
   i) generating an error signal from said ratio;
   j) integrating the error signal to produce a control signal;
   k) generating a difference signal proportional to the difference between said control signal and a reference signal; said difference signal representing the instantaneous glucose concentration in the matrix.

2. A method for determining the concentration of an analyte in the blood of a body matrix which is subject to the systolic and diastolic phases of blood flowing through the matrix during the cardiac cycle, comprising the steps of:
   a) generating a composite beam of electromagnetic radiation at each of two distinct wavelengths, a first such wavelength being analyte sensitive and a second such wavelength being analyte insensitive;
   b) directing said composite radiation at said matrix;
   c) detecting said composite radiation after it has traversed a portion of said matrix; and
   d) generating a composite electrical intensity signal proportional to the intensity of the detected composite radiation, which intensity signal is comprised of an alternating component produced by the variation in volume of blood flowing through the matrix and a non-alternating component produced by the non-varying portions of the matrix;
   e) separating the composite electrical signal into a first channel signal consisting of that portion of the electrical signal produced by detecting radiation at said first wavelength and a second channel signal consisting of that portion of the electrical signal produced by detecting radiation at said second wavelength;
   f) decomposing the first channel signal into a first alternating signal and a first non-alternating signal;
   g) decomposing the second channel signal into a second alternating signal and a second non-alternating signal;
   h) determining the difference between the value of the alternating and the non-alternating signal of each of the first and second channel signals;
   i) from said difference, determining the concentration of analyte in the matrix.

3. The method of claim 2 wherein the analyte is glucose.

4. The method of claim 3 wherein the two distinct wavelengths have the same matrix extinction in the body matrix and are in the infrared band of light.

5. A method for determining the concentration of an analyte in the blood of a body matrix which is subject to the systolic and diastolic phases of blood flowing through the matrix during the cardiac cycle, comprising the steps of:
   a) generating a composite beam of electromagnetic radiation at each of two distinct wavelengths, a first such wavelength being analyte sensitive and a second such wavelength being analyte insensitive and wherein the matrix extinction of the two wavelengths is the same in the body matrix;

b) directing said composite radiation at said matrix;
c) detecting said composite radiation after it has traversed a portion of said matrix; and
d) generating a composite electrical intensity signal proportional to the intensity of the detected composite radiation, which intensity signal is comprised of an alternating component produced by the variation in volume of blood flowing through the matrix and a non-alternating component produced by the non-varying portions of the matrix;
e) separating the composite electrical signal into a first channel signal consisting of that portion of the electrical signal produced by detecting radiation at said first wavelength and a second channel signal consisting of that portion of the electrical signal produced by detecting radiation at said second wavelength;
f) decomposing the first channel signal into a first alternating signal and a first non-alternating signal;
g) decomposing the second channel signal into a second alternating signal and a second non-alternating signal;
h) determining the amplitude ratio of the alternating to the non-alternating signal of each of the first and second channel signals;
i) from said ratio, determining the concentration of analyte in the matrix.

6. A method for determining the concentration of an analyte in the blood of a body matrix which is subject to the systolic and diastolic phases of blood flowing through the matrix during the cardiac cycle, comprising the steps of:

a) generating a composite beam of electromagnetic radiation at each of two distinct wavelengths, a first such wavelength being analyte sensitive and a second such wavelength being analyte insensitive and wherein the matrix extinction of the two wavelengths is the same in the body matrix;
b) directing said composite radiation at said matrix;
c) detecting said composite radiation after it has traversed a portion of said matrix; and
d) generating a composite electrical intensity signal proportional to the intensity of the detected composite radiation, which intensity signal is comprised of an alternating component produced by the variation in volume of blood flowing through the matrix and a non-alternating component produced by the non-varying portions of the matrix;
e) separating the composite electrical signal into a first channel signal consisting of that portion of the electrical signal produced by detecting radiation at said first wavelength and a second channel signal consisting of that portion of the electrical signal produced by detecting radiation at said second wavelength;
f) decomposing the first channel signal into a first alternating signal and a first non-alternating signal;
g) decomposing the second channel signal into a second alternating signal and a second non-alternating signal;
h) determining the difference between the value of the alternating and the non-alternating signal of each of the first and second channel signals;
i) from said difference, determining the concentration of analyte in the matrix.

7. A method for determining the concentration of glucose in the blood of a body matrix which is subject to the systolic and diastolic phases of blood flowing through the matrix during the cardiac cycle, comprising the steps of:

a) generating a composite beam of electromagnetic radiation at each of two distinct wavelengths, a first such wavelength being glucose sensitive and a second such wavelength being glucose insensitive and wherein the matrix extinction of the two wavelengths is the same in the body matrix;
b) directing said composite radiation at said matrix;
c) detecting said composite radiation after it has traversed a portion of said matrix; and
d) generating a composite electrical intensity signal proportional to the intensity of the detected composite radiation, which intensity signal is comprised of an alternating component produced by the variation in volume of blood flowing through the matrix and a non-alternating component produced by the non-varying portions of the matrix;
e) separating the composite electrical signal into a first channel signal consisting of that portion of the electrical signal produced by detecting radiation at said first wavelength and a second channel signal consisting of that portion of the electrical signal produced by detecting radiation at said second wavelength;
f) decomposing the first channel signal into a first alternating signal and a first non-alternating signal;
g) decomposing the second channel signal into a second alternating signal and a second non-alternating signal;
h) comparing the alternating to the non-alternating signal of each of the first and second channel signals;
i) from said comparison, determining the concentration of glucose in the matrix.

* * * * *